United States Patent
Mancardi et al.

(10) Patent No.: US 11,622,741 B2
(45) Date of Patent: Apr. 11, 2023

(54) SYSTEM AND METHOD FOR IMAGING A SUBJECT

(71) Applicant: GE Precision Healthcare LLC, Wauwatosa, WI (US)

(72) Inventors: Xavier Mancardi, Versailles (FR); Remy Klausz, Neuilly sur Seine (FR); Fanny Patoureaux, Beynes (FR)

(73) Assignee: GE Precision Healthcare LLC, Wauwatosa, WI (US)

( * ) Notice: Subject to any disclaimer, the term of this patent is extended or adjusted under 35 U.S.C. 154(b) by 5 days.

(21) Appl. No.: 17/334,465

(22) Filed: May 28, 2021

(65) Prior Publication Data

US 2022/0378390 A1 Dec. 1, 2022

(51) Int. Cl.
*A61B 6/00* (2006.01)

(52) U.S. Cl.
CPC .............. *A61B 6/5211* (2013.01); *A61B 6/42* (2013.01); *A61B 6/488* (2013.01); *A61B 6/5294* (2013.01); *A61B 6/582* (2013.01)

(58) Field of Classification Search
CPC ......... A61B 6/5211; A61B 6/42; A61B 6/488; A61B 6/5294; A61B 6/582; A61B 6/502; A61B 6/5258; A61B 6/545
See application file for complete search history.

(56) References Cited

U.S. PATENT DOCUMENTS

| | | | | |
|---|---|---|---|---|
| 6,292,536 B1* | 9/2001 | Chichereau | ............... | H05G 1/46 378/108 |
| 6,459,765 B1* | 10/2002 | Ganin | ................. | A61B 6/4233 378/97 |
| 7,260,171 B1* | 8/2007 | Arenson | ................. | A61B 6/06 378/19 |
| 7,313,224 B1* | 12/2007 | Saunders | ............... | A61B 6/544 378/108 |

(Continued)

FOREIGN PATENT DOCUMENTS

DE 2919425 C2 9/1984

OTHER PUBLICATIONS

Evaluation of Digital X-Ray Detectors for Medical Imaging Applicatons; Anastasios Konstantinidis; A Thesis Submitted to the University College London; London 2011; 239 pages. https://discovery.ucl.ac.uk/id/eprint/1322919/1/1322919.pdf.

(Continued)

*Primary Examiner* — Dani Fox
*Assistant Examiner* — Soorena Kefayati (57) ABSTRACT

An X-ray source transmits X-rays through a subject and a detector receives the X-ray energy after having passed through the subject. A processing system generates a pre-shot image of the subject using low energy X-ray intensity from the X-ray source and determines a plurality of acquisition parameters for a main scan of the subject based on the pre-shot image. A saturation time of the detector for the corresponding acquisition parameters is determined based (Continued)

on detector calibration data and to determine a number of time frames required to reach the targeted dose based on the saturation time. An X-ray dosage level of the subject is then applied using the X-ray source based on the number of time frames and to generate the image of the subject based on the detected X-ray energy at the X-ray detector for the applied X-ray dosage level.

18 Claims, 7 Drawing Sheets

(56) References Cited

U.S. PATENT DOCUMENTS

| | | | | |
|---|---|---|---|---|
| 7,632,016 | B1* | 12/2009 | Huang | G01T 7/005 378/207 |
| 9,230,311 | B2* | 1/2016 | Bullard | A61B 6/542 |
| 10,677,939 | B2 | 6/2020 | Jacob | |
| 10,722,187 | B2 | 7/2020 | Klausz | |
| 2005/0267348 | A1* | 12/2005 | Wollenweber | A61B 6/544 600/407 |
| 2006/0104496 | A1* | 5/2006 | Arenson | A61B 6/585 382/284 |
| 2006/0109950 | A1* | 5/2006 | Arenson | A61B 6/583 378/4 |
| 2007/0076842 | A1* | 4/2007 | Tkaczyk | A61B 6/4085 378/108 |
| 2010/0021378 | A1* | 1/2010 | Rousso | A61B 5/4076 424/1.11 |
| 2011/0243413 | A1* | 10/2011 | Tkaczyk | A61B 6/405 378/57 |
| 2012/0155609 | A1* | 6/2012 | Lemminger | A61B 6/4283 378/98.2 |
| 2013/0072781 | A1* | 3/2013 | Omernick | G16H 40/40 600/407 |
| 2014/0185762 | A1* | 7/2014 | Lee | H04N 5/32 378/62 |
| 2016/0174926 | A1* | 6/2016 | Londt | A61B 6/541 600/428 |
| 2016/0296196 | A1* | 10/2016 | Boedeker | A61B 6/032 |
| 2017/0018078 | A1* | 1/2017 | Liu | G06T 7/11 |
| 2017/0119336 | A1* | 5/2017 | Jacob | A61B 6/5258 |
| 2017/0123079 | A1* | 5/2017 | Jacob | H04N 5/32 |
| 2017/0202534 | A1* | 7/2017 | Crotty | A61B 6/465 |
| 2017/0319167 | A1* | 11/2017 | Goto | A61B 6/5211 |
| 2018/0049714 | A1* | 2/2018 | Nett | A61B 6/488 |
| 2018/0070908 | A1* | 3/2018 | Netabayashi | A61B 6/4035 |
| 2018/0088061 | A1* | 3/2018 | Nakanishi | A61B 6/027 |
| 2018/0317867 | A1* | 11/2018 | Boone | A61B 6/405 |
| 2018/0344275 | A1* | 12/2018 | Hirayama | A61B 6/463 |
| 2019/0059845 | A1* | 2/2019 | Osugi | G16H 30/20 |
| 2019/0069868 | A1* | 3/2019 | Goto | A61B 6/027 |
| 2019/0099148 | A1* | 4/2019 | Rupcich | H05G 1/26 |
| 2019/0209117 | A1* | 7/2019 | Duewer | G16H 50/20 |
| 2019/0231224 | A1* | 8/2019 | Rupcich | A61B 6/032 |
| 2019/0231296 | A1* | 8/2019 | Jackson | A61B 6/032 |
| 2019/0282194 | A1* | 9/2019 | Tkaczyk | A61B 6/4405 |
| 2020/0069261 | A1* | 3/2020 | Klausz | A61B 6/025 |
| 2020/0129137 | A1* | 4/2020 | Tsuyuki | G01T 1/17 |
| 2020/0320326 | A1* | 10/2020 | Dou | A61B 6/469 |
| 2020/0352526 | A1* | 11/2020 | Lou | A61B 6/488 |
| 2021/0251584 | A1* | 8/2021 | Nae | A61B 6/0407 |

OTHER PUBLICATIONS

Haugh, Michael & Charest, Michael & Ross, Patrick & Lee, Josh & Schneider, Marilyn & Palmer, Nathan & Teruya, Alan. (2012). Calibration of X-ray imaging devices for accurate intensity measurement. Powder Diffraction. 27. 10.1017/S0885715612000413. ; https://www.researchgate.net/publication/255250614_Calibration_of_X-ray_imaging_devices_for_accurate_intensity_measurement.

* cited by examiner

SYSTEM AND METHOD FOR IMAGING A SUBJECT

BACKGROUND

The field of the disclosure relates generally to medical technologies, and more particularly, to a system and method for imaging a subject.

Non-invasive imaging technologies allow images of the internal structures or features of a patient or a subject to be obtained without performing an invasive procedure on the patient or the subject. In particular, such non-invasive imaging technologies rely on various physical principles, such as the differential transmission of X-rays through the target volume or the reflection of acoustic waves, to acquire data and to construct images or otherwise represent the observed internal features of the patient or the subject.

For example, in computed tomography (CT) and other X-ray based imaging technologies, X-ray radiation is directed toward a subject, typically a patient in a medical diagnostic application, a package or baggage in a security screening application, or a fabricated component in an industrial quality control or inspection application. A portion of the radiation impacts a detector where the image data is collected. In digital X-ray systems, a detector generates digital signals representative of the amount or intensity of radiation impacting discrete pixel regions of the detector surface. The signals may then be processed to generate an image that may be displayed for review. In the images produced by such systems, it may be possible to identify and examine the internal structures and organs within a patient's body, objects within a package or container, or defects (e.g., cracks) within a fabricated component. In volumetric imaging systems (such as computed tomography (CT), tomosynthesis, or C-arm angiography systems) a detector array, including a series of detector elements, produces similar signals through various positions as one or both of the source and detector are displaced around the imaged volume, allowing data to be acquired over a limited or complete angular range.

In certain instances, during an X-ray exposure where a subject is being imaged but relatively little attenuation is present (e.g., due to the size, positioning, or structure of the imaged subject, such as at a skin line or tissue boundary) there is a possibility that portions of the detector array in this region of insufficient attenuation will be saturated, while other areas where more attenuation is present are not. That is, the accumulated charge at a given pixel or set of pixels may reach a limit, such that additional exposure does not result in a corresponding increase in measured charge at the pixel. Saturation leads to the loss of information and is characteristic of a detector having insufficient dynamic range to accommodate the X-ray exposure levels, in this instance a failure to accommodate the highest levels of radiation observed at imaged regions of interest, such as near the tissue edge or skin line. Therefore, there is a need for an improved X-ray imaging system and method.

BRIEF DESCRIPTION

In accordance with an embodiment of the present technique a medical imaging system is provided. The medical imaging system includes an X-ray source for transmitting X-rays through a subject and a detector to receive the X-ray energy of the X-rays after having passed through the subject. The medical imaging system further includes a processing system programmed to generate a pre-shot image of the subject using low energy X-ray intensity from the X-ray source and to determine a plurality of acquisition parameters for a main scan of the subject based on the pre-shot image. The processing system is also configured to determine a saturation time of the detector for the corresponding acquisition parameters based on detector calibration data and to determine a number of time frames required to reach the targeted dose based on the saturation time. Further, the processing system is programmed to apply an X-ray dosage level of the subject using the X-ray source based on the number of time frames and to generate the image of the subject based on the detected X-ray energy at the X-ray detector for the applied X-ray dosage level.

In accordance with another embodiment of the system, a method for imaging a subject is provided. The method includes providing an X-ray source for transmitting X-rays through a subject and providing a detector operative to receive the X-ray energy of the X-rays after having passed through the subject. The method further includes generating a pre-shot image of a subject using low energy X-ray intensity from the X-ray source and determining a plurality of acquisition parameters for a main scan of the subject based on the pre-shot image. The method also includes determining a saturation time of the detector for the corresponding acquisition parameters based on detector calibration data and determining a number of time frames required to reach the targeted dose based on the saturation time. Finally, the method includes applying an X-ray dosage level of the subject using the X-ray source based on the number of time frames and generating the image of the subject based on the detected X-ray energy at the X-ray detector for the applied X-ray dosage level.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present embodiments, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments. Furthermore, the terms "circuit" and "circuitry" and "controller" may include either a single component or a plurality of components, which are either active and/or passive and are connected or otherwise coupled together to provide the described function.

The present approaches relate to automatic exposure control (AEC) used in an X-ray imaging system. Based on a low exposure image (also referred to as pre-shot image), the AEC computes the acquisition parameters for the main acquisition that are needed to reach the required image quality. For example, in an embodiment, the pre-shot may be a low resolution two-dimensional ("2D") image acquired via a lower X-ray dose compared to subsequent X-ray dose that is used for obtaining images of the patient and used to make a medical diagnosis. The pre-shot image is also used to predict X-ray time for the main acquisition. Based on the acquisition parameters, predicted X-ray time and an X-ray detector saturation model, an additional parameter which is a number of time frames required to reach the targeted X-ray dose without saturating the detector is determined. The addition of the acquired time frames gives the resulting un-saturated image of the subject. As used herein, a subject is a human (or patient), an animal, or a phantom.

Figure 1:
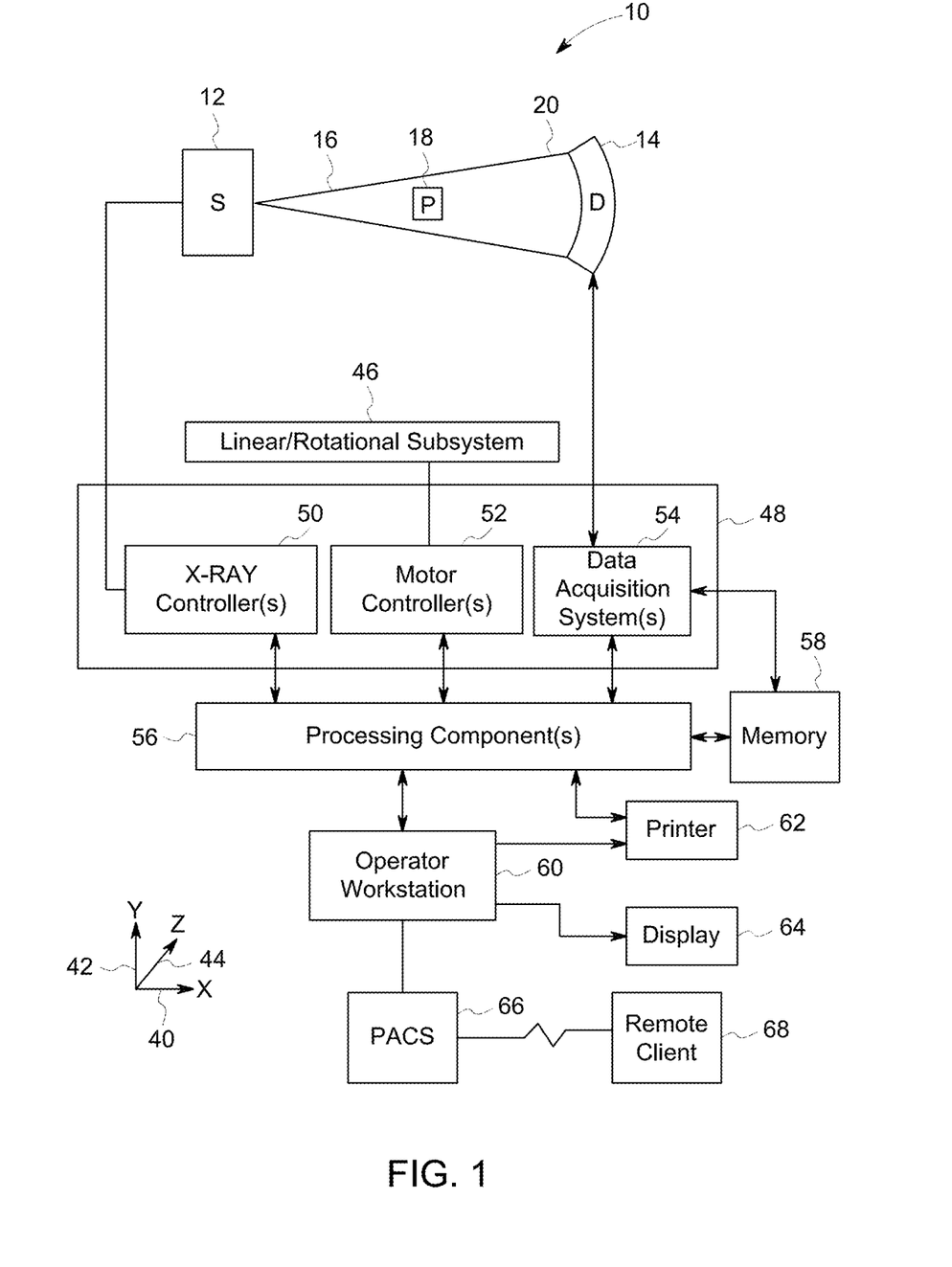
FIG. 1 is a diagrammatical view of an imaging system for use in producing images in accordance with aspects of the present disclosure.

With the preceding in mind, an example of an X-ray based imaging system 10 suitable for acquiring X-ray attenuation data for image reconstruction as discussed herein is provided in FIG. 1. In certain implementations the imaging system 10 operates so as to improve the dynamic range of the detector panel 14. For example, the detector 14 may be fabricated using complementary metal-oxide semiconductor (CMOS) materials and techniques so as to incorporate active pixels on the detector array. Such active pixels, as used herein, include amplification circuitry (e.g., an amplifier) within the respective pixel circuits themselves (as opposed to downstream and separate from the detector array) and are suitable for non-destructive readout during an imaging session. As used herein, such a non-destructive readout allows the charge at a given pixel to be inferred (i.e., read) by measuring a voltage present at the pixel at a given time. Thus, this inferred charge is determined without resetting, destroying, or otherwise losing the charge at the pixel (i.e., the pixel charge is not reset to zero). Though CMOS-based detectors are discussed in certain examples herein, it should be appreciated that the present approaches may be more generally applied to any detector capable of non-destructive readout operations, regardless of whether the fabrication of the detector utilizes CMOS components or other. Further in certain implementations the CMOS-based detector 14 is fabricated using crystalline silicon (c-Si) or amorphous silicon (a-Si).

In the embodiment illustrated in FIG. 1, imaging system 10 includes a source of X-ray radiation 12 along with the detector 14. The X-ray source 12 may be an X-ray tube, a distributed X-ray source (such as a solid-state or thermionic X-ray source) or any other source of X-ray radiation suitable for the acquisition of medical or other images. The X-rays 16 generated by the source 12 pass into a region in which a patient 18 (or an object or other subject to be imaged), is positioned during a procedure.

In the depicted example, a portion of the X-ray radiation 20 passes through or around the patient 18 (or other subject of interest) and impacts a detector array, represented generally as the detector 14. As discussed herein, detector elements (i.e., pixels) of the detector 14 produce electrical signals that represent the intensity of the incident X-rays 20. These signals are acquired and processed, as discussed herein, to reconstruct images of the features within the patient 18 or imaged object of interest.

In accordance with present embodiments, one or both of the source 12 or detector 14 may be moved (e.g., rotated and/or linearly translated) relative to the patient or imaged object along or about one or more axes during an examination procedure during which projection data is acquired. For example, the source 12 and/or detector 14 may move about one or more axes of rotation so as to facilitate acquisition of projection data at a variety of different radial views with respect to the imaged volume. Such imager motion may be supplemented by motion of the underlying patient support (e.g., table) to achieve complex imaging trajectories with respect to the relative position and motion between the imager and patient over time. In one embodiment, the translation and rotation of the imager components may be determined or coordinated in accordance with a specified protocol.

The movement of the imager components may be initiated and/or controlled by one or more linear/rotational subsystems 46. The linear/rotational subsystems 46, as discussed in further detail below, may include support structures, motors, gears, bearings, and the like, that enable the rotational and/or translational movement of the imager components. In one embodiment, the linear/rotational subsystems 46 may include a structural apparatus (e.g., a C-arm apparatus having rotational movement about at least two axes, a gantry, and so forth) supporting the source and detector 12, 14.

Other systems and subsystems may be present to support operation of the imaging components when in use. By way of example, a suitable system 10 may include a system controller 48 to coordinate and control the imaging components. Such a system controller may include one or more of an X-ray controller 50 for controlling operation of source 12, a motor controller 52 for controlling motion of movable subsystems, and a data acquisition system (DAS) 54 for handling signal readout of the detector 14. In practice, the system controller 48 may incorporate one or more processing devices that include or communicate with tangible, non-transitory, machine readable media collectively storing instructions executable by the one or more processors to perform the operations described herein.

As illustrated, the X-ray controller 50, the motor controller 52, and the data acquisition systems 54 may share one or more processing components 56 that are each specifically configured to cooperate with one or more memory devices 58 storing instructions that, when executed by the processing components 56, perform the image acquisition and reconstruction techniques described herein. Further, the processing components 56 and the memory components 58 may coordinate in order to perform the various image reconstruction processes. The system controller 48 and the various circuitry that it includes, as well as the processing and memory components 56, 58, may be accessed or otherwise controlled by an operator via an operator workstation 60. The operator workstation 60 may be communicatively coupled to a printer 62 for printing images, patient data, and the like. The operator workstation 60 may also be in communication with a display 64 that enables the operator to view various parameters in real time, to view images produced by the acquired data, and the like. The operator workstation 60 may also, in certain embodiments, be communicatively coupled to a picture archiving and communication system (PACS) 66, which may allow images to be shared with other facilities, for example, a remote client 68.

Figure 2:
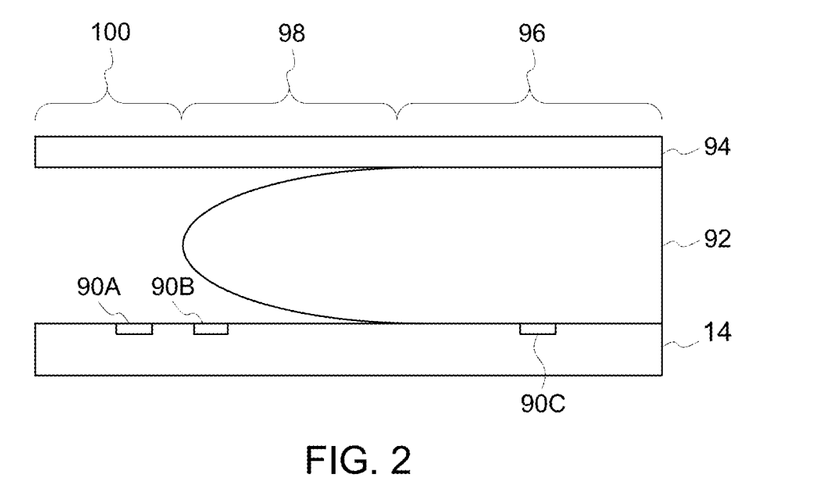
FIG. 2 is a schematic representation of a breast undergoing imaging in which X-rays are attenuated to different degrees at different points on the detector, in accordance with aspects of the present disclosure.
Figure 3:
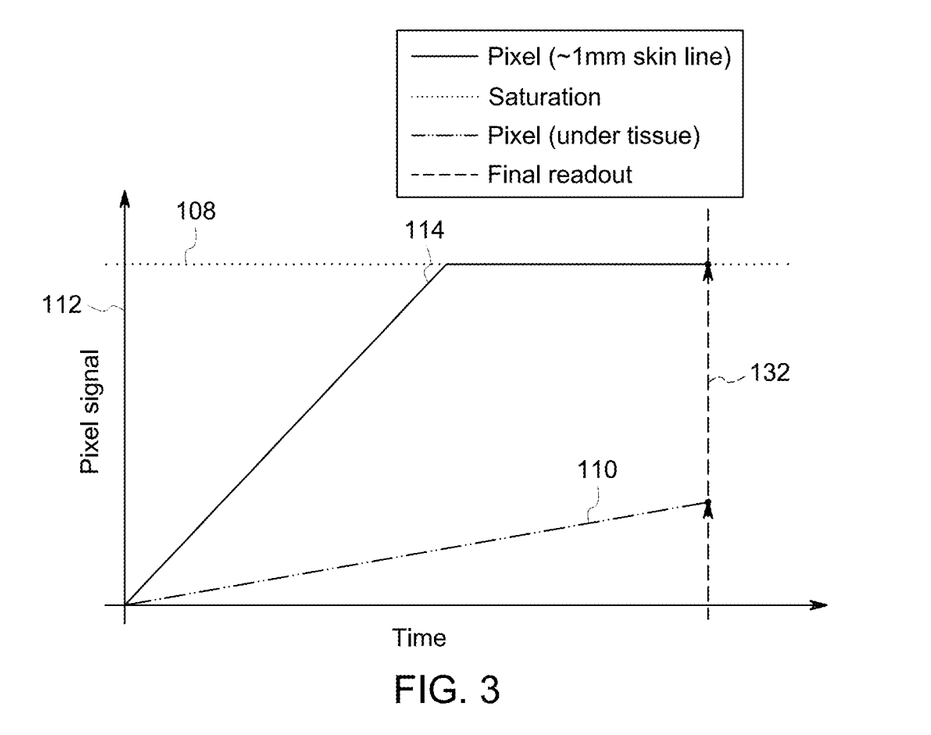
FIG. 3 graphically illustrates the charge accumulation for different pixels in a single-frame read operation.

As discussed herein, the imaging system 10, which may include a detector 14 may be used in imaging processes that address various dynamic range issues that arise in certain imaging contexts. For example, in certain circumstances one or more pixels of the detector 14 may become saturated during an exposure event. Turning to FIGS. 2 and 3 an example of such a saturation event is provided in the context of a mammography scan. In this example, a single time frame acquisition (i.e., a scan in which a single read event of the detector 14 is performed) is depicted.

As shown schematically in FIG. 2, a breast 92 to be imaged is compressed between a compression plate 94 and the detector 14 such that a portion 96 of the breast 92 is at a uniform thickness. A portion of 98 the breast 92, however, is compressed to a thinner, typically non-uniform, thickness due to the amount of tissue present. A third imaging region 100 is devoid of intervening breast tissue and is exposed to unattenuated X-rays during a scan.

Figure 4:
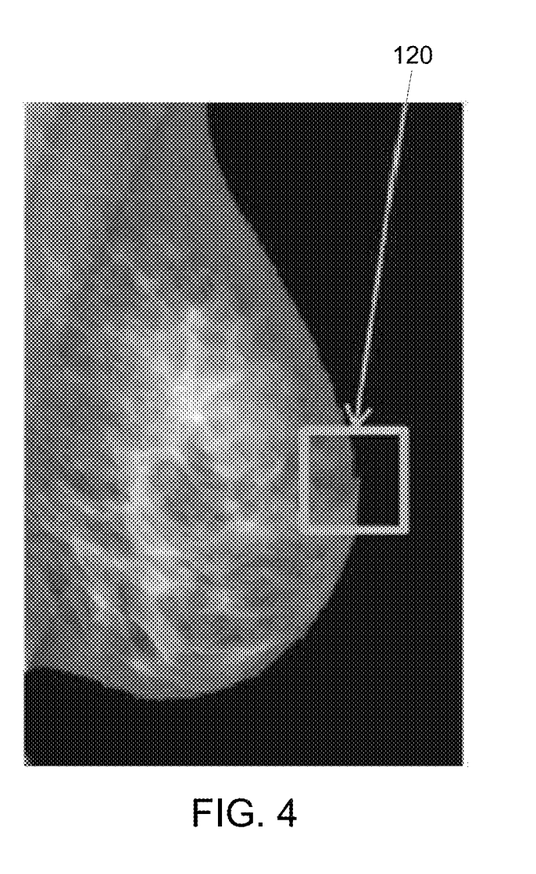
FIG. 4 is an image showing skin line artifacts present in an image generated from a single-frame acquisition.

In the depicted example three pixels 90 are shown schematically such that each pixel 90 corresponds to a respective region 96, 98, or 100 having different X-ray exposure characteristics. For example, pixel 90c, underlying the thick breast tissue region 96 receives the most attenuated X-rays and is unlikely to saturate over the exposure time (x-axis), as shown by charge accumulation line 110 and saturation threshold 108 of FIG. 3. Conversely, pixel 90a is positioned outside the boundary of the breast tissue 92 and is fully exposed to the unattenuated X-ray radiation. As a result, the pixel 90a saturates much earlier than do those pixels underneath tissue. Lastly, pixel 90b is schematically illustrated as being positioned in the vicinity of the skin line (i.e., at the tissue boundary), such that the radiation incident on the pixel 90b is partially attenuated compared to that incident on pixel 90c. That is, the X-rays incident on pixel 90b pass through some portion of tissue, and so are not unattenuated, but, as shown by charge accumulation line 114 of FIG. 2, in the scan interval associated with a single time frame read (indicated as readout 132, shown by dotted), the pixel 90b becomes saturated before the scan in completed and the pixel 90b is readout. As a result, valuable information is lost at the boundary of the imaged tissue (i.e., the skin line). This limitation with respect to the dynamic range of the detector 14 (i.e., saturation at tissue regions of interest) can result in artifacts at the skin line, such as discontinuities 120 and/or other roughness at the edges of the tissue image, as seen in FIG. 4.

Figure 5:
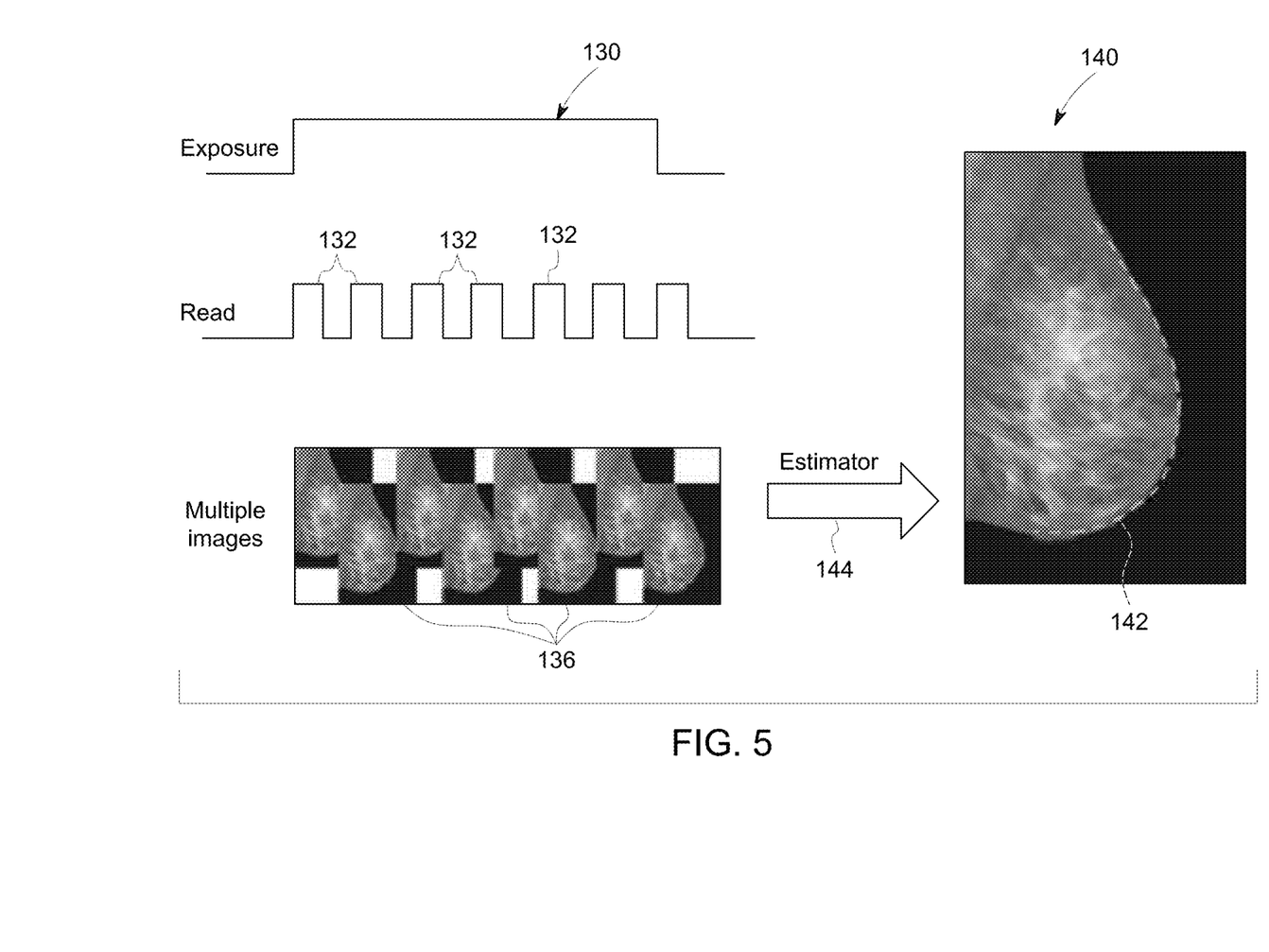
FIG. 5 depicts exposure and readout events, and corresponding images, in a multi-frame readout operation, in accordance with aspects of the present disclosure.

One approach to address saturation issues for regions where the tissue is of non-uniform thickness and where attenuation is less than what is seen for thicker tissue regions being imaged is described with reference to FIGS. 5 and 6. In this approach multiple destructive (i.e., charge depleting) readout operations are performed over the course of a single scan exposure. This is graphically illustrated in FIG. 5, where an exposure event 130 occurs over a time t. Over the course of the exposure 130, multiple destructive readout operations 132 (also referred to as multiple time frames) are performed, with readout events generally timed so as to avoid saturation of pixels in those areas of the detector panel underlying tissue regions where uniform thickness cannot be achieved (e.g., near the tissue boundary within the image and so forth). Each readout operation 132 or time frame generates attenuation data that can be reconstructed into a separate image 136. Some or all of the multiple images 136 can be combined or summed to generate a final image 140 with reduced skin line artifacts. Alternatively, as shown in FIG. 5, some or all of the multiple images may be used in an estimation process 144 in which various image parameters (e.g., the skin line boundary, electronic noise, signal-to-noise, optimized pixel intensity) are estimated and used to generate a final or diagnostic image. For example, in one implementation, the skin line boundary (dotted line 142) may be estimated and the final image may include pixels populated with intensity data up to the boundary so as to minimize data loss at the boundary region.

Figure 6:
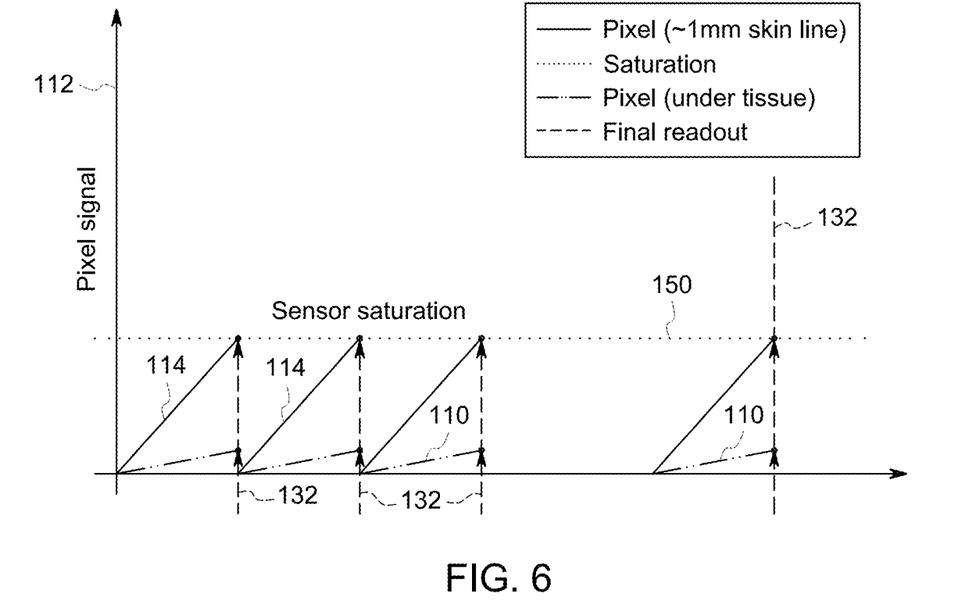
FIG. 6 graphically illustrates the charge accumulation for different pixels in a multi-frame readout operation, in accordance with aspects of the present disclosure.

Turning to FIG. 6, a graphical representation of pixel charge accumulation for such a multi-frame embodiment is shown which is similar to the graphical representation of FIG. 3 and which is based on the pixel arrangement shown in FIG. 2. In this example pixel 90c, underlying the thick breast tissue region 96 receives the most attenuated X-rays and does not saturate between readout events 132, as shown by charge accumulation lines 110 and sensor saturation threshold 150. Pixel 90a is positioned outside the boundary of the breast tissue 92 and is fully exposed to the unattenuated X-ray radiation. As a result, the pixel 90a saturates much earlier than do those pixels underneath tissue, even in this multi-frame scenario. Pixel 90b is schematically illustrated as being positioned in the vicinity of the skin line (i.e., at the tissue boundary), such that the radiation incident on the pixel 90b is partially attenuated compared to that incident on pixel 90c. As shown by charge accumulation lines 114 of FIG. 6, in the scan intervals associated with multiple readout events 132, the pixel 90b approaches saturation but, even if saturation is reached, does not spend substantial time in the elapsed state before being readout and the charge cleared. As a result, attenuation information is generally not lost at the boundary of the imaged tissue (i.e., the skin line) or in the regions where the tissue thickness is less than the uniformly compressed regions.

As will be appreciated, the depicted example is idealized and, in practice, the charge accumulation lines 114 may reflect that the readout events occur prior to the pixel 90b reaching saturation threshold 150 or, alternatively, some minimal amount of time may be spent in a saturated state before readout for these pixels 90b. However, due to general retention of attenuation data at the skin line, the summing or estimation processes employed to construct final image 140 from the multiple images 136 may reflect a generally expanded or extended dynamic range for the detector 14.

In accordance with an embodiment of the present technique, an automatic exposure control (AEC) algorithm is used to generate relevant acquisition parameters needed for main scan of the patient. It should be noted that the main scan event here refers to the image acquisition of the patient based on which the patient disorder diagnosis is determined. The AEC algorithm controls the X-ray exposure per image and helps avoid saturation of the detector 14 and may be implemented in X-ray controller 50 of FIG. 1. In general, the preferred embodiment of the AEC algorithm utilizes a pre-shot image from detector 14. The pre-shot image is obtained from a small dose of X-rays occurring before the main X-ray exposure that results in an image of a patient. A plurality of acquisition parameters is then determined from the pre-shot image. The plurality of acquisition parameters includes X-ray tube current, X-ray tube voltage, targeted X-ray dose etc. An additional parameter-saturation time of the detector is determined using a calibration method. Based on the plurality of acquisition parameters and the saturation time of the detector, a number of time frames or scan events required to reach the targeted dose without saturating the detector are determined.

Figure 7:
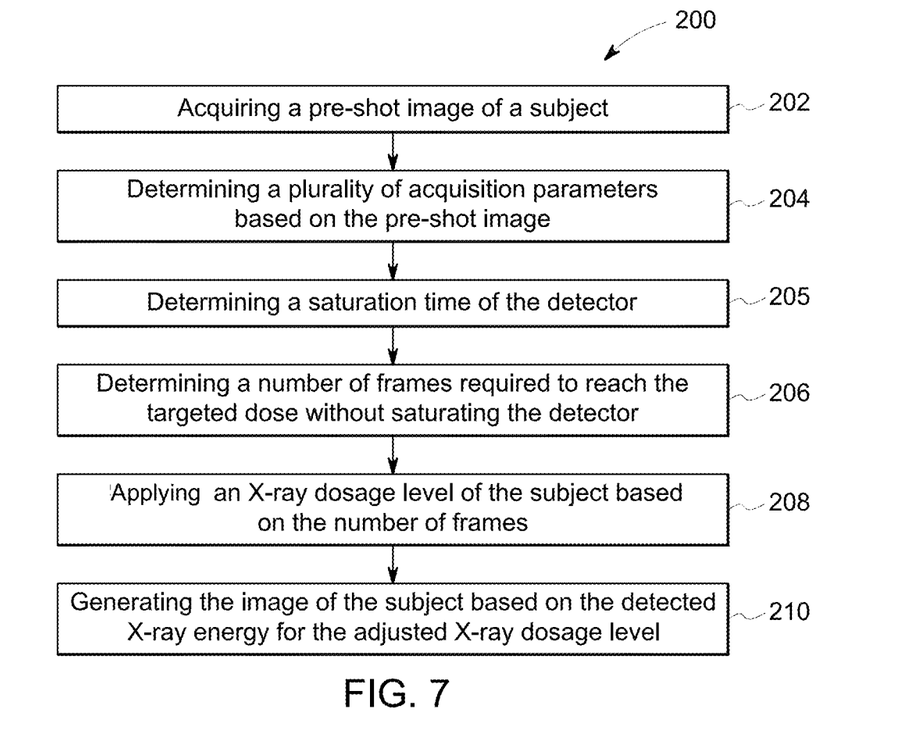
FIG. 7 is a flow chart depicting a method for imaging a subject in accordance with an embodiment of the present technique.

FIG. 7 shows a flow chart 200 of a method for imaging a subject in accordance with an embodiment of the present technique. The method includes acquiring a pre-shot image of the subject in step 202. As explained earlier, the pre-shot image is obtained from a small dose of X-rays before the main X-ray exposure of the subject that results in an image of the subject obtained for diagnosis. At step 204, the method includes determining a plurality of acquisition parameters based on the pre-shot image. The plurality of acquisition parameters includes X-ray tube current, X-ray tube voltage, and targeted X-ray dose of the detector among others.

In one embodiment, determining the acquisition parameter may be based on configuration settings determined while taking the pre-shot image such as one of an anode material of the X-ray source, a peak kilovoltage ("kVp") of the X-ray source, a milliamperes ("mA") per pulse of the X-ray source, i.e., the integral of a current flowing through a ray tube/generator of the source during a pulse which may be in milliampere-seconds ("mAs"). As will be understood, in embodiments, the acquisition parameters may be derived from the configuration settings via one or more models, e.g., a look up table containing values for anode material, filter selection, kVp, mAs per pulse and/or time.

In step, 205, a saturation time for the detector corresponding to the plurality of acquisition parameters is determined based on detector calibration data. It should be noted that the detector calibration data obtained by pre-calibrated the detector in advance of the main scan of the subject. In general, there are at a plurality of settings in the X-ray system—X-ray tube voltage (kV), X-ray tube anode material (track), and material used for X-ray beam filtration (filter), X-ray source current (mA), targeted X-ray dosage (mAs). To calibrate the detector, the naked detector 14 (i.e., without the subject to be scanned) is illuminated by the X-ray source 12 in every possible configuration setting of X-ray system 10. For each of these configuration settings and a corresponding X-ray tube current, the time at which the detector saturates is determined. In one embodiment the saturation time may be determined by dividing the saturation scan total exposure by the saturation scan tube current. Thus, saturation times for various configuration settings of the X-ray system 10 are stored in a look up table and at the time of the main scan of the subject, the look up table provides the saturation time corresponding to the plurality of acquisition parameters.

Based on the plurality of acquisition parameters and the saturation time, a number of time frames or scan events required to reach the targeted dose without saturating the detector are determined in step 206. At step 208, the method includes applying an X-ray dosage level of the subject based on the number of time frames. The X-ray dosage level is applied by X-ray source 12 based on the X-ray controller commands which provides the number of time frames. Finally, at step 210, the image of the subject is generated based on the detected X-ray energy for the applied X-ray dosage level.

Figure 8:
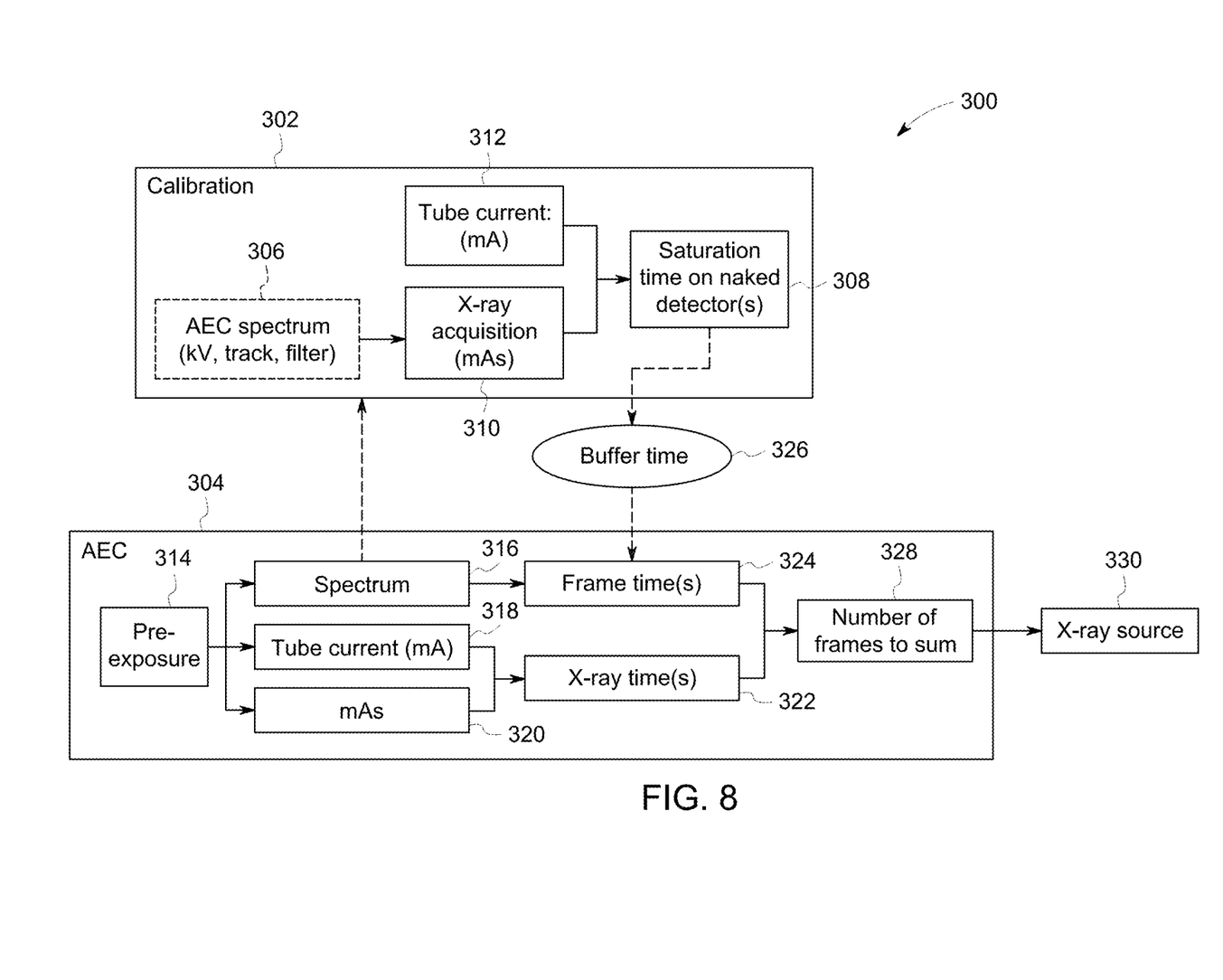
FIG. 8 is a schematic diagram depicting a portion of the imaging system of FIG. 1.

FIG. 8 shows a schematic diagram 300 of a portion of imaging system 10 of FIG. 1. In one embodiment, the portion 300 is part of the X-ray controller 50 of FIG. 1. X-ray controller 50 includes a calibration module 302 and an AEC acquisition module 304. As used herein, the term "module" refers to software, hardware, or firmware, or any combination of these, or any system, process, or functionality that performs or facilitates the processes described herein.

In general, as discussed earlier, there are at least three settings in the X-ray system—X-ray tube voltage (kV), X-ray tube anode material (track), and material used for X-ray beam filtration (filter) which are varied to apply the X-ray dosage of the subject according to the thickness and density (e.g., breast thickness and density). In one embodiment, the calibration module 302 illuminates the naked detector 14 (i.e., without the subject to be scanned) by the X-ray source 12 in every possible configuration of these three settings. In another embodiment, instead of illuminating the naked detector in every possible configuration, only a few configuration points are considered and an interpolation from only those points of measure is considered. The AEC spectrum 304 of all these configuration points is provided to calibration module 302 as an input.

Calibration module 302 determines a saturation time 308 of the detector 14 for each of the configuration settings (kV, track, filter). In one embodiment, to determines the saturation time 308, calibration module 302 first measures the saturation scan total exposure (mAs) 310 which is the X-ray exposure at which the detector saturates for the given configuration setting. Thereafter, the calibration module 302 measures the saturation scan tube current (mA) 312 that was applied and then based on the tube current mA and the saturation scan total exposure the saturation time 308 is determined. In one embodiment the saturation time 308 may be determined by dividing saturation scan total exposure by the saturation scan tube current (i.e., mAs/mA). Thus, saturation times for various configuration settings of the X-ray system 10 are stored in a look up table by the calibration module 302.

The AEC module 304 first acquires a pre-shot or pre-exposure image 314 which is used to measure the attenuation property of the subject. In certain embodiments, the attenuation property is polymethyl methacrylate-equivalent thickness at densest location of the subject. The pre-shot image is generated based on low energy X-ray intensity exposure of the subject from the X-ray source. It should be noted here that the low energy X-ray intensity here refers to the X-ray intensity which has a lower value compared to the X-ray intensity used for main scan of the subject. As will be appreciated by those skilled in the art, based on the low exposure scan results, it is possible to determine how much X-ray radiation is being attenuated (i.e., attenuation properties) by the subject. Once the attenuation properties are determined then based on the attenuation properties of the subject, the spectrum values 316, tube current 318 and total exposure 320 for the main scan can be determined. Spectrum values 316 includes configuration settings (kV, track, filter) for the main scan. AEC module 304 then provides the configuration settings 306 to the calibration module 302, which determines saturation time 308 from the look up table corresponding to the configuration settings 306.

Further, main scan total exposure (mAs) 320 and main scan tube current (mA) 318 are also determined from the attenuation properties of the subject. In one embodiment, based on the main scan tube current 318 and the main scan total exposure 320, main scan X-ray time 322 is determined. For example, the main scan X-ray time 322 may be determined by dividing main scan total exposure 320 value by the main scan tube current 318 value. AEC module 304 further determines a time frame 324 by subtracting a buffer time 326 from the saturation time 308 corresponding to the same configuration as that of main scan configuration. The buffer time 326 is used to provide some extra time margin to integrate the whole signal from the main x-ray acquisition. Finally, a number of time frames 328 required for main scan acquisition are determined based on time frame 324 and X-ray time 322. In one embodiment, the number of time frames 328 may be determined by dividing X-ray time 322 by time frame 324. The plurality of time frames as determined by the number 328 are then used to apply X-ray dosage level of the subject using the X-ray source 330 for acquiring the main scan and to generate the image of the subject for disorder diagnosis.

Figure 9:
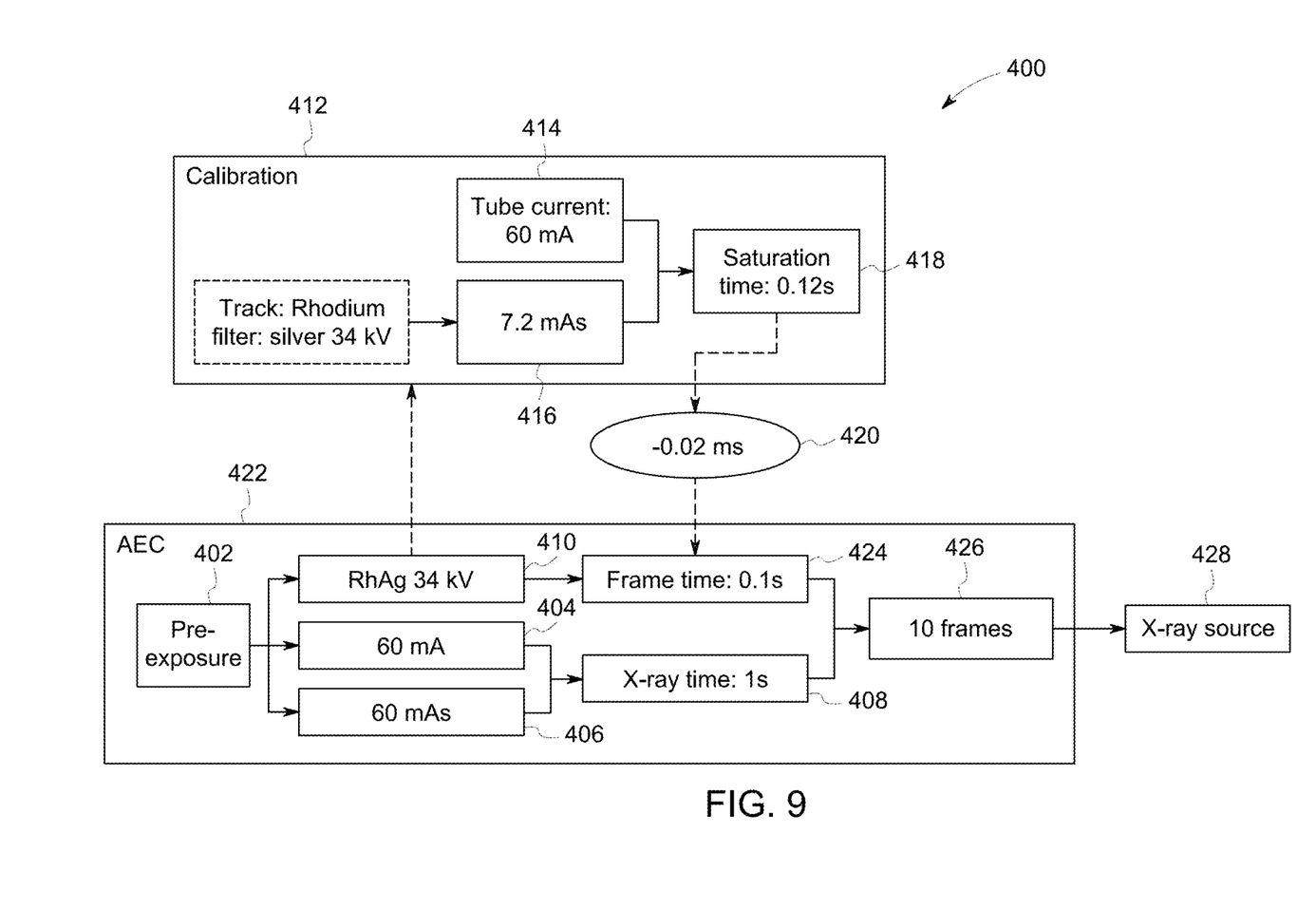
FIG. 9 is a schematic diagram depicting an example time frame calculation of FIG. 8.

FIG. 9 shows a schematic diagram 400 of an example time frame calculation system of FIG. 8. As can be seen from schematic 400, based on pre-shot image 402, AEC acquisition module 422 determines the main scan tube current 404 to be 60 mA and main scan total exposure 406 to be 60 mAs. Further, based on the main scan tube current 404 and the main scan total exposure 406, the X-ray time 408 is determined to be (60 mAs/60 mA=) 1 second. Moreover, based on pre-shot image 402, main scan configuration settings 410 are determined to be X-ray tube voltage=34 kV, filter=Silver and track=Rhodium. These main scan configuration settings 410 are provided to calibration module 412 which determines that for given X-ray tube current 414 (60 mA), the detector X-ray saturation exposure 416 occurs at 7.2 mAs. Thus, based on X-ray tube current 414 and X-ray saturation exposure 416, the saturation time 418 is determined to be 0.12 seconds.

In the schematic diagram 400, the buffer time is set as 0.02 seconds. Accordingly, AEC acquisition module 422 determines a time frame 424 equal to (0.12 s−0.02 s=) 0.1 seconds. Finally, a total number of time frames 426 are determined by dividing X-ray time 408 (1 seconds) by the time frame 424 (0.1 seconds) which is equal to 10 time frames. These 10 time frames are then applied to the X-ray source 428 to generate the image of the subject for diagnosis.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A medical imaging system comprising:
 an X-ray source operative to transmit X-rays through a subject;
 a detector operative to receive an X-ray energy of the X-rays after having passed through the subject; and
 a processing system programmed to:
  generate a pre-shot image of the subject using low energy X-ray intensity from the X-ray source;
  determine a plurality of acquisition parameters for a main scan of the subject based on the pre-shot image;
  determine a saturation time of the detector for each of the plurality of acquisition parameters based on detector calibration data;
  determine a number of time frames required to reach a targeted dose based on the saturation time;
  apply an X-ray dosage level of the subject using the X-ray source based on the number of time frames;
  generate an image of the subject based on the detected X-ray energy at the detector for the applied X-ray dosage level;
 wherein the detector calibration data is predetermined in advance of the main scan; and
 wherein the processing system is programmed to determine calibration data by illuminating the detector without the subject in a plurality of configuration settings of the medical imaging system and recording the saturation time for each of the plurality of configuration settings in a look up table.

2. The medical imaging system of claim 1, wherein the processing system is programmed to determine the plurality of acquisition parameters by determining an attenuation property of the subject based on the pre-shot image.

3. The medical imaging system of claim 1, wherein the plurality of configuration settings includes every possible configuration setting of the imaging system or less than a total number of configuration settings of the medical imaging system.

4. The medical imaging system of claim 1, wherein the processing system is programmed to record the saturation time for each of the plurality of configuration settings by dividing a saturation scan total exposure by a corresponding X-ray source current.

5. The medical imaging system of claim 1, wherein the plurality of acquisition parameters includes a X-ray source current (mA), a X-ray source voltage (kV), targeted X-ray dosage (mAs), X-ray tube anode material (track), and material used for X-ray beam filtration (filter).

6. The medical imaging system of claim 2, wherein the attenuation property includes polymethyl methacrylate-equivalent thickness at a densest location of the subject.

7. The medical imaging system of claim 3, wherein when the plurality of configuration settings includes less than the total number of configuration settings of the medical imaging system, remaining configuration setting in the look up table are obtained based on an interpolation from the plurality of configuration settings used for illuminating the detector.

8. The medical imaging system of claim 5, wherein the processing system is programmed to determine the number of time frames required to reach the targeted dose based on a frame time and a main scan X-ray time.

9. The medical imaging system of claim 8, wherein the processing system is programmed to determine the frame time by subtracting a buffer time from the saturation time.

10. The medical imaging system of claim 8, wherein the processing system is programmed to determine the main scan X-ray time by dividing the targeted X-ray dosage (mAs) by the X-ray source current (mA).

11. A method for imaging a subject comprising:
providing an X-ray source operative to transmit X-rays through a subject;
providing a detector operative to receive an X-ray energy of the X-rays after having passed through the subject;
generating a pre-shot image of a subject using low energy X-ray intensity from the X-ray source;
determining a plurality of acquisition parameters for a main scan of the subject based on the pre-shot image;
determining a saturation time of the detector for each of the plurality of acquisition parameters based on detector calibration data;
determining a number of time frames required to reach a targeted dose based on the saturation time;
applying an X-ray dosage level of the subject using the X-ray source based on the number of time frames;
generating an image of the subject based on the detected X-ray energy at the detector for the applied X-ray dosage level; and
wherein the method further comprises determining the detector calibration data by illuminating the detector without the subject in every possible configuration setting of the medical imaging system and recording the saturation time for every possible configuration setting in a look up table.

12. The method of claim 11 comprising determining the plurality of acquisition parameters by determining an attenuation property of the subject based on the pre-shot image.

13. The method of claim 11 comprising recording the saturation time for each of the configuration setting by dividing a saturation scan total exposure by a corresponding X-ray source current.

14. The method of claim 11, wherein the plurality of acquisition parameters includes a X-ray source current (mA), a X-ray source voltage (kV), targeted X-ray dosage (mAs), X-ray tube anode material (track), and material used for X-ray beam filtration (filter).

15. The method of claim 14 further comprising determining the number of time frames required to reach the targeted dose based on a frame time and a main scan X-ray time.

16. The method of claim 15 comprising determining the frame time by subtracting a buffer time from the saturation time.

17. The method of claim 15 comprising determining the main scan X-ray time by dividing the targeted X-ray dosage (mAs) by the X-ray source current (mA).

18. A medical imaging system comprising:
an X-ray source operative to transmit X-rays through a subject;
a detector operative to receive an X-ray energy of the X-rays after having passed through the subject; and
a processing system programmed to:
generate a pre-shot image of the subject using low energy X-ray intensity from the X-ray source;
determine a plurality of acquisition parameters for a main scan of the subject based on the pre-shot image;
determine a saturation time of the detector for each of the plurality of acquisition parameters based on detector calibration data;
determine a number of time frames required to reach a targeted dose based on the saturation time;
apply an X-ray dosage level of the subject using the X-ray source based on the number of time frames;
generate an image of the subject based on the detected X-ray energy at the detector for the applied X-ray dosage level;
wherein the plurality of acquisition parameters includes a X-ray source current (mA), a X-ray source voltage (kV), targeted X-ray dosage (mAs), X-ray tube anode material (track), and material used for X-ray beam filtration (filter);
wherein the processing system is programmed to determine the number of time frames required to reach the targeted dose based on a frame time and a main scan X-ray time; and
wherein the processing system is programmed to determine the frame time by subtracting a buffer time from the saturation time.

* * * * *